United States Patent [19]

Herkes

[11] 4,283,306

[45] Aug. 11, 1981

[54] CRYSTALLINE SILICA AND USE IN ALKYLATION OF AROMATICS

[75] Inventor: Frank E. Herkes, Wilmington, Del.

[73] Assignee: E. I. Du Pont de Nemours and Company, Wilmington, Del.

[21] Appl. No.: 129,272

[22] Filed: Mar. 26, 1980

Related U.S. Application Data

[63] Continuation-in-part of Ser. No. 032,001, Apr. 20, 1979.

[51] Int. Cl.³ .............................................. B01J 21/02
[52] U.S. Cl. .................................. 252/432; 252/437; 252/449; 252/454; 252/456; 252/457; 423/328; 423/339; 585/467
[58] Field of Search ............... 252/432, 437, 449, 454, 252/456, 457; 423/328, 339

[56] References Cited

U.S. PATENT DOCUMENTS

| Re. 29,948 | 3/1979 | Dwyer et al. ...................... 260/429.9 |
| 4,002,698 | 1/1977 | Kaeding ................................ 585/454 |
| 4,038,211 | 7/1977 | Frampton ............................ 252/437 |
| 4,064,070 | 12/1977 | Harrison ............................... 252/437 |
| 4,073,865 | 2/1978 | Flanigan et al. ..................... 423/339 |

Primary Examiner—Curtis R. Davis

[57] ABSTRACT

Novel crystalline silicas and their use as alkylation catalysts, e.g., methylation of toluene. The performance of the catalysts can be improved by selected promoters.

10 Claims, No Drawings

CRYSTALLINE SILICA AND USE IN ALKYLATION OF AROMATICS

RELATED APPLICATIONS

This application is a continuation-in-part of copending application U.S. Ser. No. 032,001 filed on Apr. 20, 1979.

BACKGROUND OF THE INVENTION

1. Field of the Invention

A novel crystalline silica polymorph and its use, with or without promoters, as a catalyst for the alkylation of aromatics e.g., the methylation of toulene to para-xylene.

2. Description of the Prior Art

Aluminosilicate zeolites are known as catalysts for the methylation of toulene. U.S. Pat. No. 3,965,208, U.S. Pat. No. 4,100,215, U.S. Pat. No. 4,127,616, and Yashima et al, "Alkylation On Synthetic Zeolites", Journal of Catalysis, 16, 273 to 280 (1970), are representative of the art which describes zeolites as catalysts for toulene methylation.

It is known from OS No. 2,755,770 that all or part of the alumina in an aluminosilicate zeolite can be replaced by iron oxide or by iron oxide in combination with gallium oxide. The OS states that the described metallosilicates are useful as catalysts in the methylation of toulene. The OS, therefore, broadens the store of knowledge concerning zeolites useful in methylation of toulene by suggesting the utility of iron-containing metallosilicates.

The interrelationship of the alumina (or alumina substitute) and silica contents of zeolites relevant to their utility in the toulene methylation process has apparently not been studied. However, U.S. Pat. No. 3,894,103 explores the silica/alumina ratio relevant to the use of zeolites as catalysts in converting lower aliphatic alcohols such as methanol to aromatic compounds. From the Table bridging columns 5 and 6 of U.S. Pat. No. 3,894,103 it is clear that the amount of aromatic product produced decreases as the silica/alumina ratio is increased. At a ratio of 35/1 the amount of aromatic product produced is 77% or 79%; see columns 1 and 2 of the Table. At a ratio of 1300/1 no aromatic product is produced; see column 10 of the Table. The data presented in this patent would lead one to conclude that high ratios of silica to alumina are generally detrimental to catalytic activity. Thus, one would not expect very much activity of crystalline silica in the catalysis of a toulene methylation reaction.

Several crystalline silica compositions, both with and without promoters, are known. See, for instance: U.S. Pat. No. 3,941,871, U.S. Pat. No. 4,061,724, U.S. Pat. No. 4,073,865, U.S. Pat. No. 4,104,294, and Flanigen et al, "Silicalite, A New Hydrophobic Crystalline Silica Molecular Sieve", Nature, Vol. 271, Feb. 9, 1978, pages 512 to 516.

Only in U.S. Pat. No. 4,104,294, however, is there any intimation that crystalline silica compositions might be useful as catalysts. The statement that such compositions are suitable for use in "hydrocarbon conversion" reactions is nonspecific, unexplained, and unsupported. Therefore, the patent does little to propel one skilled in the art to use crystalline silica as a catalyst since the weight of authority is that such a material would, at best, be a poor catalyst. The statement concerning the extensive area of "hydrocarbon conversion" does nothing to teach the art that such catalysts would have utility in toulene methylation or, in fact, in any specific transformation process.

Against the background of the prior art as described heretofore, it has now been found that a novel crystalline silica containing substantially no alumina or alumina-substitute in the crystal lattice is an excellent catalyst for the specific process of methylating toluene to produce xylene, which process is characterized by particularly high proportions of the para-isomer.

SUMMARY OF THE INVENTION

A crystalline silica polymorph having essentially clear intracrystalline channels with axes in the range 5.0–6.5, preferably about 5.0–5.8 Ångstrom units and a density in the range 1.81–1.94 preferably 1.83–1.89 gms/ml. This silica is further characterized by X-ray diffraction whereby the width at one-half height of the diffraction peak at $d(A) = 3.00 \pm 0.05$ being in the range of about $0.05° - 0.210°$ $(2\theta)$ and more particularly, also at $d(A) = 1.46 \pm 0.05$ being in the range of about $0.05° - 0.320°$ $(2\theta)$. The peak to background ratio at $d(A) = 3.85 \pm 0.03$ is at least about 20 and preferably at least 30.0.

An additional aspect of the present invention is an improved process for producing para-xylene by the catalytic methylation of toluene. The improvement resides primarily in the use of crystalline silica compositions, with or without promoters, as the catalysts. Contemplated promoters include arsenic oxide, phosphorus oxide, boron oxide, antimony oxide, amorphous silica, alkaline earth metal oxides, carbonates and precursors thereof e.g., magnesium, calcium, barium, strontium, beryllium, carbonates and oxides precursors and mixtures thereof, said promoter(s) being present in an amount from 0 to about 50%, preferably 0.3% to 25%, based on total weight of metal oxide or carbonate in the catalyst. Preferred promoters are boron oxide, antimony oxide, calcium oxide, calcium carbonate and amorphous silica. The most preferred promoters are amorphous silica and calcium carbonate.

The mole ratio of toluene to methylating agent in the reactant feed can vary between about 1 to 50/1 respectively. Preferred ratios are 3 to 30/1 and the most preferred ratios are 5 to 20/1. Reactant ratios richer in methylating agent than about 1 part per part of toluene may lead to the formation of undesirable by-products. Reactant ratios richer in toluene than about 50 parts per part of methylating agent may lead to high energy costs to separate the para-xylene and recycle the reactants.

The rate of reactant feed, in terms of weight hourly space velocity, WHSV, is the weight of reactant feed per weight of catalyst per hour. WHSV may vary between about 1 to 500. Preferably, reactant feeds will vary between 2 to 250 and most preferably between 3 to 100.

DETAILED DESCRIPTION OF THE INVENTION

The novel crystalline silica polymorph of the present invention has a lattice comprising silica; it is microporous, having a pore size or intracrystalline channel size (axes) in the range 5.0–6.5 Angstron units. These pores or intracrystalline channels are essentially clear, i.e., they are not obstructed by molecules, atoms or ions such as chlorine, sodium, nitrate and sulfate, etc. which can be present in crystalline silicas of the prior art and which hinder transport to internal sites. Density and crystallinity measured as set forth hereinbelow are other distinguishing features of this novel silica. The measured density of the silica of the present invention closely approximates the theoretical (calculated) density indicating that, unlike the crystalline silicas of the prior art, the silica of the present invention exhibits a minimum of crystal defects with a significant number of acid sites. Although this novel crystalline silica may contain small amounts of alumina, iron or germanium impurities adsorbed or occluded therein, such materials do not form any regular part of the lattice network and therefore the silica cannot be considered a metallosilicate.

The crystalline silica in its activated form after calcination at 550° C. in air for 4 hours has a specific gravity (density) of 1.81–1.94 and preferably 1.83–1.89 gm/cc as measured by water displacement. This high specific gravity (density) is believed to be one indication of good catalyst performance.

The crystalline silica, after heating in air at 550° C. for at least about 2 hours displays a characteristic X-ray powder diffraction pattern having its strongest lines at interplanar d spacings (Å) and relative intensities ($I/I_o$) substantially as set out in Table A.

TABLE A

| Å | $I/I_o$ |
|---|---|
| 3.85 ± 0.05 | 100 |
| 11.1 ± 0.2 | 87 |
| 3.81 ± 0.05 | 57 |
| 9.93 ± 0.1 | 51 |
| 3.71 ± 0.05 | 49 |
| 3.79 ± 0.05 | 45 |
| 9.80 ± 0.1 | 42 |
| 3.74 ± 0.05 | 40 |
| 3.00 ± 0.05 | 38 |
| 5.95 ± 0.1 | 30 |
| 2.01 ± 0.05 | 25 |
| 1.99 ± 0.05 | 25 |
| 3.65 ± 0.05 | 20 |
| 3.61 ± 0.05 | 20 |
| 2.95 ± 0.05 | 18 |
| 1.46 ± 0.05 | 17 |

The X-ray diffraction measurements are obtained with CuK$\alpha$ radiation at 40 KeV 35 m at a maximum rate of 2500 ct/sec on a recording Phillips diffractometer having a scintillation counter and compensating slits containing 12.5 mm of irradiated sample 3 mils in thickness. Peak heights, I, and positions as a function of 2 times theta ($\theta$) where theta is the Bragg angle, were measured. From these values, relative intensities and interplanar d spacings were calculated.

The width at one-half of the diffraction peak height (WH/2) is measured at one or two locations in the X-ray pattern (obtained as above). The first measurement is made at $d(Å)=3.00\pm0.05$ and is in the range of about 0.05°–0.210° ($2\theta$) and the second is made at $d(Å)=1.46\pm0.05$ and is in the range of about 0.05°–0.320° ($2\theta$). These measurements are distinguishing characteristics of the silicas of the present invention. Another distinguishing measurement is the peak to background ratio which is given by the expression A−B/B wherein A is the number of counts per second of the most intensive reflection in the X-ray diffraction pattern of the sample (according to the above-described procedure) and B is the counts per second at a non-diffracting angle between 15°–18° ($2\theta$) using ¼° ($2\theta$) per minute scanning rate on a non-preferentially ordered sample. The silicas of the present invention exhibit a peak to background of at least 20, preferably at least 30 and in some instances greater than 40.

The crystalline silica of this invention is made by heating a reaction mixture containing water, a silica-source, such as silica sols, alkali metal silicates, silica gels, fumed silicas, etc., and an alkylonium compound, such as quaternary ammonium or phosphonium salts, under hydrothermal conditions at a pH of 10 to 14. The pH can be controlled with alkali metal hydroxide. Heating is continued until crystalline silica is formed. Typical reaction temperatures and times for crystalline silica formation are 120° to 200° C. for about 20 to 200 hours but preferably 150°–165° C. from 30 to 120 hours. The product is then separated from the liquid by filtration, washed with water, and dried at 95° to 105° for 8 to 16 hours. The crystalline silica is characterized by the X-ray powder diffraction pattern shown in Table A.

Crystalline silica obtained by the procedure of the preceding paragraph is catalytically inactive until activated in air or $N_2$ at about 200° C. to 550° C. for about 4 hours followed by base exchange with ammonium salts, such as ammonium nitrate, followed by calcination in air or $N_2$ for several hours at about 200° C. to 550° C. A third heating sequence (thermal activation) at about 200° to 600° C. in air or $N_2$ is necessary if the activated crystalline silica is treated with a promoter or promoter precursor. This third heating sequence is employed after such treatment and before use.

As will be appreciated by those skilled in the art, time and temperature are interrelated so that, within the spirit of the disclosure presented herein, activation temperatures and other temperatures, may exceed those set out if heating times are correspondingly reduced. Likewise, somewhat lower temperatures may be employed if heating times are correspondingly increased.

The crystalline silica of the present invention, preferably in an active form, can be combined with one or more promoters by an appropriate technique selected from one or more of the following: impregnation, adsorption, physical mixing, chemical reaction, or coating. Reaction of the active crystalline silica with arsenic-, phosphorus-, magnesium-, boron-, calcium-, antimony-, and silicon-containing promoters is effected by contacting the activated crystalline silica with any of these compounds in their oxide or carbonate precursor form. Suitable compounds include arsenic (III) butoxide, triethylphosphate, magnesium oxide, boric oxide, trimethylborate, antimony oxide, antimony (III) butoxide, calcium nitrate, strontium nitrate, alkaline earth metal organic acid salts, silanes and silicones. The oxide and precursors can be used to contact the crystalline silica while in the form of liquids, solutes in solution, solids or gases. Acid catalysts to enhance the silylation process can also be employed. Examples include trifluoroacetic acid and p-toluenesulfonic acid.

The silanes have the general formula:

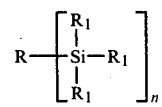

where n is 1 or 2; R is a reactive group such as hydrogen, alkoxy, halogen, carboxy, amino, and acetamide; $R_1$ can be the same as R; or $R_1$ can be an alkyl of 1 to about 40 carbon atoms; an alkyl or aryl carboxylic acid wherein the alkyl group contains about 1 to 30 carbon atoms and the aryl group contains about 6 to 24 carbon atoms; an aryl of about 6 to 24 carbons which may be further substituted; or an alkaryl or aralkyl containing about 7 to 30 carbon atoms. Preferably, the alkyl group of an alkyl silane has from 1 to 4 carbon atoms and the carbon chain of an alkoxy group has from 1 to 6 carbon atoms. Alkoxy-containing silanes are preferred. One such preferred alkoxy-containing silane is tetraethoxysilane (ethylorthosilicate). Mixtures of the above compounds can also be used.

The silicone compounds have the general formula:

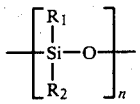

where $R_1$ is hydrogen, fluorine, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, other than hydrogen, and $n$ is an integer of at least 10 and generally in the range of 10 to 1000. The molecular weight of the silicone compound employed is generally between about 500 to 20,000 and preferably within the approximate range of 1000 to 10,000. Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethylsilicone, tetrachlorophenylethylsilicone, tetrachlorophenylhydrogensilicone, tetrachlorophenylphenylsilicone, methylvinylsilicone and ethylvinylsilicone. Phenylmethylsilicone is preferred.

The promoter can be in the form of a liquid, gas or solid. A solvent can be employed to dissolve the promoter, followed by contact with the crystalline silica. Any solvent which is inert to reaction with the promoter can be used, including water, alcohols, and aliphatic or aromatic hydrocarbons. The promoter can also be used neat, by soaking or admixture with the crystalline silica or by gaseous deposition.

The promoter oxides or precursors, used neat or dissolved in a suitable solvent such as n-hexane, benzene, toluene, xylene, chloroform or carbon tetrachloride, are contacted with the activated crystalline silica between 25° C. and 100° C. for a period of time sufficient to deposit the desired amount of promoter thereon. The contact time will usually vary from 1 to 16 hours. Solvent, if used, is then removed by filtration or evaporation. The promoted crystalline silica is then dried at 95° to 125° C. in nitrogen or air for several hours. Activation of promoted crystalline silica is achieved by calcination at temperatures up to about 600° C. Preferably, the calcination temperature is raised slowly, e.g., 1 to 10° C./min until about 600° C. is reached and then held for a time sufficient to complete the activation.

Gaseous promoter oxides are contacted with the activated crystalline silica between 300°–500° C. for a period of time sufficient to deposit the desired amount of promoter which is 0.3 to 24 wt %. This is usually controlled by the rate of feed and contact time. Final activation of the promoted crystalline silica may or may not be required prior to the alkylation reation.

The silicas of the present invention are useful as catalysts for several reactions including the alkylation of aromatics and particularly for the methylation of toluene.

Typical methylating agents include methanol, dimethylether, methylchloride, methylbromide and dimethylsulfide. One skilled in the art will know that other methylating agents may be employed in the process of this invention based on the description provided herein. Preferred methylating agents are methanol and dimethylether. Methanol is most preferred.

The methylation process is characterized by high yields of xylene based on toluene and methylating agent, as well as surprisingly high specificity to para-xylene at the expense of the ortho and meta isomers.

Of the xylene isomers, i.e., ortho-, meta- and para-xylene, the latter is of particular value being useful in the manufacture of terephthalic acid which is an intermediate in the manufacture of synthetic fibers including those bearing the Dacron ® trademark. Mixtures of xylene isomers generally contain about 24 weight percent para-xylene in the equilibrium mixture. Para-xylene is usually separated from such mixtures by expensive superfraction and multistage refrigeration steps. The process of this invention affords a xylene product in which paraxylene predominates. The improved yield of paraxylene, up to a fourfold increase over the 24 percent equilibrium concentration, reduces the cost of production and separation of para-xylene from the ortho- and meta-isomers.

The characteristic high yields of para-xylene are believed to result from selectivity of the crystalline silica catalyst to an alkylation mechanism. The alkylation resulting in high para-selectivity is believed to take place inside the pore structure while the crystal surface reaction sites, which can give rise to undesired side products via isomerization, disproportionation, alkyl exchange, and reactions of methylating agent with itself, are of relatively low activity. The use of promoters further enhances the product contribution from the alkylation occurring inside the pores versus the undesirable surface reactions. Presence of other metals, e.g., aluminum, as an intrinsic part of prior art crystalline catalysts is associated with excessive reactivity to form undesired side products. Particularly undesirable is the reaction of methylating agent to olefins and alkanes thereby decreasing para-xylene yield based on methylating agent.

The methylation process can be carried out as a batch type, semi-continuous or continuous operation utilizing a fixed or moving bed catalyst system. Multiple injection of the methylating agent may be employed. One embodiment entails use of a fluidized catalyst zone wherein the reactants are passed concurrently or countercurrently through a moving fluidized bed of the catalyst. The catalyst, of course, can be regenerated after use.

Toluene and methylating agent are usually premixed and fed together into the reaction vessel to maintain the desired ratio between them with no local concentration of either reactant to disrupt reaction kinetics. Individual feeds can be employed, however, if care is taken to insure good mixing of the reactant vapors in the reaction vessel. Instantaneous concentration of methylating agent can be kept low by staged additions thereof. By staged additions, toluene/methylating agent concentrations can be maintained at optimum levels to give good toluene conversions. Hydrogen gas can be supplied to the reaction as an anticoking agent and diluent.

The catalyst and reactants can be heated to reaction temperature separately or together. Reaction temperatures are about 400° C. to 650° C., preferably about 500° C. to 600° C., and most preferably about 550° C. Higher temperatures than about 650° C. may cause disproportionation, coking, and dealkylation; lower temperatures than about 400° C. will slow the reaction rate.

Reaction pressures can vary from subatmospheric to superatmospheric. Pressures between about 50 kPa and 4,000 kPa or higher are operable; preferred pressures are 100 kPa to 2,000 kPa. As pressures increase, the amount of ortho- or meta-xylene isomer may increase.

In practicing the alkylation process, it may be desirable to incorporate the crystalline silica in another material resistant to alkylation temperatures and conditions. Such matrix materials include synthetic or naturally occurring substances as well as inorganic materials such as clay, silica and metal oxides. The latter may be either naturally occurring or in the form of gelatinous precipitates or gels including mixtures of silica and metal oxides. Naturally occurring clays which can be composited with the crystalline silica include those of the montmorillonite and kaolin families. The matrix can be in the form of a cogel. The relative proportions of finely divided crystalline silica and inorganic oxide gel matrix can vary widely with the crystalline silica content ranging from about 1 to 90 percent by weight and more usually in the range of about 2 to 70 percent by weight of the composite.

The following Examples are presented to illustrate but not to restrict the present invention. Parts and percentages are by weight unless otherwise noted.

EXAMPLE 1

Crystalline silica catalyst was prepared from the following reactants:

| | |
|---|---|
| $(C_2H_5)_4NCl$ | 115.3 |
| NaOH | 30.4 |
| $H_2O$ | 108 |
| 30% $SiO_2$ | 1270 |

The 30% $SiO_2$ was obtained as Ludox® SM a 30% dispersion of colloidal silica in water containing small amounts of sodium impurity.

An aqueous solution of the $(C_2H_5)_4NCl$ and the NaOH was mixed vigorously for 15 minutes at room temperature with the colloidal silica. This resultant mixture was charged to a 1 gallon titanium autoclave. The autoclave was sealed and the temperature of the contents was raised to 150° C. at 10°/min with slow (75 to 95 RPM) stirring and held for 60 hrs at 150° C. with slow stirring following which the slurry was discharged from the autoclave and filtered.

The solid crystalline product on the filter was washed with water to remove unreacted salts and soluble reactants and was then dried at 95° C. in nitrogen.

X-ray analyses establishes the material as 100% crystalline silica. Analysis of a dried sample was as follows:

| Compound | % |
|---|---|
| N | 0.96 |

-continued

| Compound | % |
|---|---|
| C | 6.5 |
| $Na_2O$ | 0.76 |
| $Al_2O_3$ | 518 (ppm) |
| Balance $H_2O$ and $SiO_2$ | |

This crystalline silica was calcined in air at 550° C. for 4 hours and then exchanged with ammonium by contacting two successive times at 95° C. with 10% $NH_4NO_3$ solution (1 gram per 10 grams of crystalline silica), first for 16 hours and then for 4 hours. The catalyst precursor was then filtered, washed with $H_2O$, dried at 95° C. in $N_2$, and calcined (activated) in air for 4 hours at 550° C. The measured peak to background ratio for the $d(Å)=3.85$ peak was 53. Diffraction peaks at $d(Å)=3.00$ and $d(Å)=1.46$ have widths at half heights of 0.20 and 0.17° ($2\theta$) respectively. An observed density of 1.86 g/cc was found by water displacement.

EXAMPLE 2

Crystalline silica catalyst was prepared from the following reactants:

| | |
|---|---|
| $(C_2H_5)_4NCl$ | 576 g |
| NaOH | 152 g |
| $H_2O$ | 540 g |
| 30% $SiO_2$ | 6350 g. |

The 30% $SiO_2$ was obtained as Ludox® SM a 30% dispersion of colloidal silica in water containing small amounts of sodium impurity.

An aqueous solution of $(C_2H_5)_4NCl$ and NaOH was mixed vigorously for 15 minutes at 35° C. with the colloidal silica. This mixture was charged to a 3 gallon Hastelloy C autoclave and sealed. The temperature of the vessel was raised to 160° C. at 10°/min with slow (75 to 95 RPM) stirring and held for 4 days at 160° C. with slow stirring.

The solid crystalline product was filtered from the slurry and washed with water to remove unreacted salts and soluble reactants. It was then dried at 95° C. in nitrogen.

X-ray analyses established the material as 100% crystalline silica. Analysis of a dried sample was as follows:

| Compound | % |
|---|---|
| N | 0.70 |
| C | 5.26 |
| $Na_2O$ | 0.63 |
| $H_2O$ | 1.2 |
| $SiO_2$ | 92.2 |
| $Al_2O_3$ | 508 (ppm) |

The crystalline silica was calcined in air at 550° C. for 4 hours and then exchanged with ammonium by contacting two successive times at 95° C. with 10% $NH_4NO_3$ solution (1 gram per 10 grams of crystalline silica), first for 16 hours and then for 4 hours. The catalyst precursor was then filtered, washed with $H_2O$, dried at 95° C. in $N_2$, and calcined (activated) in air for 4 hours at 550° C. The surface area after activation was 320 m$^2$/g.

EXAMPLE 3

A catalyst consisting of crystalline silica having an amorphous coating of silica was prepared in the following manner. Crystalline silica, prepared by the procedure of Example 2, in the amount of 75 grams was stirred in a solution of 13.2 grams of ethyl orthosilicate in 880 ml of n-hexane at 25° C. for 2 to 3 hours. The solvent was slowly removed on a rotary evaporator and dried at 95° C. in $N_2$. The catalyst was activated by heating to 500° C. according to this procedure:

25° to 120° C., then 1 hour at that temperature,
120° to 200° C., then 1 hour at that temperature,
200° to 250° C., then 1 hour at that temperature,
250° to 350° C., then 1 hour at that temperature,
350° to 400° C., then 1 hour at that temperature,
400° to 450° C., then 1 hour at that temperature,
450° to 500° C., then 5 hours at that temperature.

The theoretical amount of silica deposited was 5% based on total weight of metal oxides in the catalyst.

EXAMPLE 4

A catalyst was prepared by stirring 100 grams of crystalline silica, prepared by the procedure of Example 2, in a solution of 21.5 grams of boric acid and 250 ml of $H_2O$ at 80° C. for 16 hours. The mixture was concentrated to a paste and dried at 100° C. in $N_2$. Activation of the catalyst was performed by heating it in air at 200° C. for 2 hours, then at 500° C. for 16 hours. The concentration of boric oxide on crystalline silica was 9% based on total weight of metal oxides in the catalyst.

EXAMPLE 5

Crystalline silica, prepared by the procedure of Example 2, in the amount of 8.5 grams, was added to a solution of 1.5 grams of ethylorthosilicate in 100 ml of n-hexane. The mixture was stirred for 1 hour at 25° C. followed by removal of solvent on a rotary evaporator. The catalyst precursor was dried at 95° C. in nitrogen followed by the slow calcination described in Example 3 except that the activated catalyst was kept at 500° C. for 4 hours and not 5 hours. The amount of silica deposited was about 5% based on total weight of metal oxides in the catalyst.

EXAMPLE 6

Crystalline silica, prepared by the procedure of Example 2, in the amount of 50 grams was added to a solution of 50 grams of antimony (III) butoxide in 300 ml of dry xylene and refluxed for 16 hours under nitrogen. The cooled mixture was filtered under nitrogen and washed with toluene, methanol and petroleum ether. The catalyst precursor was air dried at room temperature for two hours and then heated at 95° C. in nitrogen for two days. The catalyst was formed into pellets of 3/16 inch and calcined for 4 hours at 500° C.

EXAMPLE 7

An amount of 133 grams of crystalline silica, prepared by the procedure of Example 2, was stirred in a solution of 28.6 grams of boric acid and 333 ml of distilled water at 80° C. for 16 hours. The slurry was transferred to an evaporating dish and concentrated to a paste on a hot plate. The mixture was dried in nitrogen at 100° C. followed by heating in air at 200° C. for 2 hours and then 500° C. for 16 hours. The calcined catalyst contained approximately 10% of $B_2O_3$ based on the total weight of metal oxides in the catalyst.

EXAMPLE 8

Crystalline silica was prepared from the following reactants:

| | |
|---|---|
| $(C_2H_5)_4NCl$ | 57.6 g |
| NaOH | 15.2 |
| $H_2O$ | 140 g |
| fumed $SiO_2$ | 190 g. |

The fumed $SiO_2$ was obtained as Cab-O-sil® HS-5.

An aqueous solution of $(C_2H_5)_4NCl$ and NaOH (in 55 ml of water) was added to a mixture of 190 grams of fumed silica and 855 ml of water with vigorous stirring at 25° C. The mixture was stirred for an additional 15 minutes until a homogeneous mix resulted. The mixture was charged to a 4-liter titanium autoclave and sealed. The temperature of the vessel was raised to 160° C. at 10°/min with slow stirring and maintained at 160° C. for 60 hours. The solid crystalline product was filtered and washed to remove the soluble salts. The product was dried in nitrogen at 95° C.

Product analysis of a dried sample was:

| Compound | % |
|---|---|
| $[(C_2H_5)_4N]_2O$ | 9.62 |
| $H_2O$ | 1.05 |
| $Na_2O$ | 0.43 |
| $Al_2O_3$ | 365 (ppm) |
| $SiO_2$ | 88.9 |

The crystalline silica was calcined in air at 550° C. for 4 hours and exchanged with ammonium by contacting two successive times at 95° C. with 10% $NH_4NO_3$ solution, first for 16 hours and then for 4 hours. The exchanged catalyst was filtered, washed with $H_2O$ and dried at 95° C. in nitrogen. Final activation was performed at 550° C. for 4 hours in air.

EXAMPLE 9

Crystalline silica, prepared by the procedure of Example 2, in the amount of 20 g., was added to a solution of 2.5 grams of a phenylmethyl diphenyl silicone (MW 8000) in 200 ml of n-hexane. The mixture was stirred for 16 hours at 25° C. followed by removal of solvent on a rotary evaporator. The catalyst precursor was dried at 95° C. in nitrogen followed by the slow calcination described in Example 3.

EXAMPLE 10

Crystalline silica, prepared by the procedure of Example 2, in the amount of 42.5 g, was added to a solution of 7.5 g of ethylorthosilicate in 500 ml of n-hexane. The mixture was stirred for 1 hour at 25° C. followed by removal of solvent on a rotary evaporator. The catalyst precursor was dried at 95° C. in $N_2$ followed by the slow calcination described in Example 3. The calcined catalyst was mixed with a second solution of 7.5 g of ethylorthosilicate in 500 ml of n-hexane for 2 hours at 25° C. The catalyst precursor, after removal of solvent and drying in $N_2$ at 95° C., was activated a second time employing a slow calcination in air at 25° C. to 525° C. at incremental increases of 2°/min, then at 525° C. for 4 hours.

The activated catalyst was mixed with montmorillonite clay and water (60% crystalline silica, 40% montmorillonite binder on ignited basis) and then extruded to form 1/16 inch pellets. The pellets were dried at 95° C. in $N_2$ for 8 hours prior to use.

EXAMPLE 11

Crystalline silica, prepared by the procedure of Example 2, in the amount of 9 g was stirred in a solution of 2.0 g of phenylmethylsilicone (MW 4000) in 100 ml of n-hexane at 25° C. for 1 hour. The solvent was removed on a rotary evaporator. The catalyst precursor was then activated in air at 25° C. to 540° C. at incremental increases of 1°/min, then at 540° C. for 7 hours.

EXAMPLE 12

Crystalline silica, prepared by the procedure of Example 2, was added to a solution of ethylorthosilicate in 100 ml of n-hexane. The weights of crystalline silica and ethylorthosilicate were caried to yield a deposition weight of $SiO_2$ ranging from 0.5 to 18 weight percent. The weight of crystalline silica to volume of hexane ranged from 0.08 to 0.10. The mixture was stirred for 1 hour at 25° C. followed by removal of solvent on a rotary evaporator. Each sample of coated catalyst was then activated by heating to 550° C. at 10°/min followed by heating for 7 hours in air at 550° C.

EXAMPLE 13

Crystalline silica, prepared by the procedure of Example 2, was added to a solutionof ethylorthosilicate in 100 ml of n-hexane. The weights of crystalline silica and ethylorthosilicate were varied to yield a deposition weight of $SiO_2$ ranging from 0.3 to 5 weight percent. The weight of crystalline silica to volume of hexane ranged from 0.085 to 0.099. The mixture was stirred for 1 hour at 25° followed by removal of solvent on a rotary evaporator. The catalysts were then dried at 95° C. in $N_2$ for 16 hours followed by activation as described in Example 3.

EXAMPLE 14

Crystalline silica (50 g), prepared by the procedure of Example 1, was added to a solution containing 42 g ethyl orthosilicate and 2 g of trifluoroacetic acid in 417 ml toluene. The mixture was stirred and refluxed for 2 hours followed by cooling to 40°. An equal volume of petroleum ether was added and the mixture filtered under nitrogen. The catalyst was washed an additional time with petroleum ether and dried under $N_2$. The catalyst was then activated by heating to 550° C at 1°/min, followed by heating for 7 hours at 550°.

EXAMPLE 15

A 70:30 wt: wt % mixture consisting of 50 g crystalline silica prepared according to Example 1 and 21 g bentonite were intimately dry mixed for 1 hour on a roller mill. The powder was mixed with water to make a pasty dough and molded into 1/8 inch pellets. The pellets were dried at 95° followed by calcination at 550° for 2 hous.

EXAMPLE 16

Crystalline silica (6 g), prepared by the procedure of Example 1, was added to a solution containing 5 g ethyl orthosilicate in 50 ml toluene. The reaction conditions and work-up were similar to that described in Example 14. The catalyst was activated by heating to 550° at 1°/min, followed by heating for 7 hours at 550°.

EXAMPLES 17 to 19

An amount of 3.6 g of the catalyst of Example 2 was placed in a 1 inch diameter quartz reactor inserted in a split-tube furnace and employed in three successive methylations of toluene to paraxylene. A 3/1 mole ratio of toluene to methanol together with a concurrent hydrogen ($H_2$) feed, in a ratio of $H_2$ to hydrocarbon (HC) of 0.8, was passed over the powder catalyst at 101 kPa (1 atm.). The reaction conditions and results expressed in mole percent are summarized in Table 1.

TABLE 1

| Ex. No. | Toluene/ MeOH | Weight Hourly Space Velocity | Temp. °C. | Mole Percent Conversion | | Percent Para Selectivity In Xylene |
|---|---|---|---|---|---|---|
| | | | | Toluene | MeOH | |
| 17 | 3 | 3.9 | 450 | 14.6 | 88 | 56 |
| 18 | 3 | 3.9 | 500 | 19.6 | 95 | 53 |
| 19 | 3 | 3.9 | 550 | 26.3 | 95 | 51 |

EXAMPLES 20 TO 25

An amount of 3.6 grams of the catalyst of Example 5 was charged to a 1 inch diameter quartz reactor and employed in six successive catalytic methylations of toluene at 101 kPa. A solution of toluene and methanol along with a feed of $H_2$ ($H_2$/HC=0.8) was passed over the catalyst under the conditions and with the results summarized in Table 2.

TABLE 2

| Ex. No. | Toluene/ MeOH | Weight Hourly Space Velocity | Temp. °C. | Mole Percent Conversion | | Percent Para Selectivity In Xylene |
|---|---|---|---|---|---|---|
| | | | | Toluene | MeOH | |
| 20 | 3 | 3.9 | 450 | 13.4 | 99 | 94 |
| 21 | 3 | 3.9 | 500 | 16.6 | 99 | 93 |
| 22 | 3 | 3.9 | 550 | 18.8 | 99 | 93 |
| 23 | 3 | 3.9 | 600 | 20.1 | 99 | 92 |
| 24 | 10 | 3.9 | 500 | 8.4 | 99 | 93 |
| 25 | 10 | 3.9 | 550 | 9.6 | 99 | 91 |

EXAMPLES 26 TO 28

An amount of 3.6 grams of the catalyst of Example 6 was charged to a 1 inch diameter quartz reactor and employed in three successive toluene methylations. A 3/1 mole ratio of toluene to methanol together with a feed of $H_2$ ($H_2$/HC=0.8) was passed over the catalyst pellets at 101 kPa under the reaction conditions and with the results summarized in Table 3.

TABLE 3

| Ex. No. | Toluene/ MeOH | Weight Hourly Space Velocity | Temp. °C. | Mole Percent Conversion | | Percent Para Selectivity In Xylene |
|---|---|---|---|---|---|---|
| | | | | Toluene | MeOH | |
| 26 | 3 | 4.4 | 450 | 8.6 | 90 | 72 |
| 27 | 3 | 4.4 | 500 | 14.9 | 90 | 72 |
| 28 | 3 | 4.4 | 550 | 19.3 | 90 | 75 |

EXAMPLES 29-39

Amounts of the catalyst of Example 7 were placed in a 1 inch diameter quartz reactor and employed at 101 kPa under the reaction conditions and with the results summarized in Table 4. An anticoking/diluent feed of $H_2$ ($H_2/HC=0.8$) was also employed.

TABLE 4

| Ex. No. | Toluene/ MeOH | Weight Hourly Space Velocity | Temp. °C. | Mole Percent Conversion Toluene | MeOH | Percent Para Selectivity In Xylene |
|---|---|---|---|---|---|---|
| 29[1] | 3 | 2.5 | 450 | 14.7 | 99 | 82 |
| 30[1] | 3 | 2.5 | 500 | 18.6 | 99 | 82 |
| 31[1] | 3 | 2.5 | 550 | 20.9 | 99 | 81 |
| 32[2] | 3 | 3.9 | 500 | 18.1 | 99 | 82 |
| 33[3] | 3 | 9.4 | 550 | 21.5 | 88 | 75 |
| 34[2] | 5 | 3.9 | 500 | 12.2 | 94 | 87 |
| 35[4] | 3 | 1.0 | 550 | 18.1 | 99 | 88 |
| 36[2] | 10 | 3.9 | 550 | 8.7 | 99 | 90 |
| 37[5] | 3 | 3.9 | 500 | 7.7 | 70 | 97 |
| 38[5] | 3 | 3.9 | 550 | 9.5 | 77 | 99 |
| 39[5] | 3 | 3.9 | 600 | 8.3 | 80 | 98 |

[1]The number of grams of catalyst was 5.7.
[2]The number of grams of catalyst was 3.6.
[3]The number of grams of catalyst was 1.5.
[4]The number of grams of catalyst was 13.5.
[5]The catalyst, 3.6 grams, was steamed at 550° C. for 3 hours under 3% $H_2O$ in nitrogen.

EXAMPLES 40 TO 44

Catalysts prepared by the process of Example 12 were tested for the methylation of toluene along with a $H_2$ feed ($H_2/HC=0.8$) at 101 kPa. The results and reaction conditions are summarized in Table 5.

TABLE 5

| Ex. No. | SiO$_2$ Coating Weight Percent | Weight Hourly Space Velocity | Mole Percent Conversion Toluene | MeOH | Percent Para Selectivity In Xylene |
|---|---|---|---|---|---|
| 40 | 0.5 | 5.4 | 9.4 | 99 | 75 |
| 41 | 1.0 | 5.6 | 9.1 | 99 | 70 |
| 42 | 5.0 | 5.4 | 8.4 | 99 | 86 |
| 43 | 10.0 | 6.4 | 8.2 | 99 | 93 |
| 44 | 18.0 | 7.4 | 8.0 | 99 | 94 |

EXAMPLES 45 TO 48

An amount of 3.6 g of the catalyst of Example 2 was charged to a 1 inch diameter quartz reactor and tested for the methylation of toluene employing a 10/1 toluene/methanol feed along with a hydrogen feed ($H_2/HC=0.8$) at 101 kPa pressure.

TABLE 6

| Ex. No. | Temp. °C. | Weight Hourly Space Velocity | Mole Percent Conversion Toluene | MeOH | Percent Para Selectivity In Xylene |
|---|---|---|---|---|---|
| 45 | 500 | 3.9 | 8.2 | 99 | 43 |
| 46 | 550 | 3.9 | 9.1 | 99 | 47 |
| 47 | 550 | 7.8 | 8.3 | 95 | 66 |

TABLE 6-continued

| Ex. No. | Temp. °C. | Weight Hourly Space Velocity | Mole Percent Conversion Toluene | MeOH | Percent Para Selectivity In Xylene |
|---|---|---|---|---|---|
| 48 | 550 | 15.6 | 6.5 | 77 | 72 |

EXAMPLES 49 TO 56

An amount of 3.6 g of the catalyst of Example 9 was charged to a 1 inch diameter quartz reactor and tested in toluene methylation employing a concurrent $H_2$ feed. The reaction conditions and results are summarized in Table 7.

TABLE 7

| Ex. No. | Weight Hourly Space Velocity | Temp. °C. | $\frac{H_2}{HC}$ Ratio | $\frac{Tol}{MeOH}$ Mole | Mole Percent Conversion Toluene | MeOH | Percent Para Selectivity In Xylene |
|---|---|---|---|---|---|---|---|
| 49 | 3.9 | 550 | 0.8 | 3 | 19.2 | 99 | 84 |
| 50 | 3.9 | 600 | 0.8 | 3 | 20.0 | 99 | 84 |
| 51 | 3.9 | 500 | 0.8 | 20 | 5.0 | 99 | 81 |
| 52 | 3.9 | 550 | 0.8 | 20 | 5.6 | 99 | 81 |
| 53 | 3.9 | 500 | 0.8 | 10 | 8.3 | 99 | 84 |
| 54 | 3.9 | 550 | 0.8 | 10 | 9.4 | 99 | 84 |
| 55 | 7.8 | 550 | 0.4 | 10 | 8.4 | 99 | 83 |
| 56 | 15.6 | 550 | 0.2 | 10 | 7.9 | 99 | 92 |

EXAMPLES 57 TO 60

An amount of 3.6 g of the catalyst of Example 5 was charged to a 1 inch diameter quartz reactor and employed in four successive toluene methylations at 101 kPa pressure employing a 3/1, toluene/methanol, mole ratio. A concurrent feed of $H_2$ ($H_2/HC=0.8$) was employed.

TABLE 8

| Ex. No. | Weight Hourly Space Velocity | Temp. °C. | Mole Percent Conversion Toluene | MeOH | Percent Para Selectivity In Xylene |
|---|---|---|---|---|---|
| 57 | 3.9 | 450 | 13.4 | 99 | 94 |
| 58 | 3.9 | 500 | 16.6 | 99 | 93 |
| 59 | 3.9 | 550 | 19.7 | 99 | 93 |
| 60 | 3.9 | 600 | 20.1 | 99 | 92 |

EXAMPLES 61 TO 63

An amount of 3.6 g of 1/16 inch extrudate catalyst of Example 10 was charged to a 1 inch diameter quartz reactor and tested for its methylation activity with toluene. A feed of 10/1, toluene/methanol, along with a concurrent feed of hydrogen ($H_2/HC=0.8$) was employed at a space velocity of 3.9 hr$^{-1}$ and 101 kPa pressure. The reaction conditions and results are summarized in Table 9.

TABLE 9

| Ex. No. | Temp. °C. | Mole Percent Conversion Toluene | Methanol | Percent Para Selectivity In Xylene |
|---|---|---|---|---|
| 61 | 450 | 5.8 | 99 | 89 |
| 62 | 500 | 7.5 | 99 | 90 |
| 63 | 550 | 8.1 | 99 | 89 |

EXAMPLES 64 TO 66

An amount of 2.5 g of the catalyst of Example 11 was charged to a quartz microreactor and tested for its ability to alkylate toluene employing dimethylether (Me$_2$O) as the methylating agent. A 5.4/1 mole ratio of toluene to dimethylether along with a concurrent feed of H$_2$ (H$_2$/toluene of 0.8) was passed over the catalyst at 101 kPa pressure and a space velocity of 5.3 hr$^{-1}$ based on toluene fed. The results and reaction conditions are summarized in Table 10.

TABLE 10

| Ex. No. | Temp. °C. | Mole Percent Conversion Toluene | Mole Percent Conversion Me$_2$O | Percent Para Selectivity In Xylene |
|---|---|---|---|---|
| 64 | 450 | 19.1 | 80 | 88 |
| 65 | 500 | 18.0 | 91 | 87 |
| 66 | 550 | 21.0 | 93 | 88 |

EXAMPLES 67–69

An amount of 3.6 g of the catalyst of Example 8 was charged to a 1 inch diameter quartz reactor and tested for the methylation of toluene employing a 10/1 mole ratio of toluene/methanol feed along with a hydrogen feed (H$_2$/HC=0.8) at 101 kPa. The reaction conditions and results are summarized in Table 11.

TABLE 11

| Ex. No. | Temp. °C. | Mole Percent Conversion Toluene | Mole Percent Conversion MeOH | Percent Para Selectivity In Xylene |
|---|---|---|---|---|
| 67 | 450 | 4.9 | 80 | 80 |
| 68 | 500 | 6.2 | 84 | 75 |
| 69 | 550 | 7.1 | 87 | 70 |

EXAMPLES 70–75

An amount of 3.6 g of the silica promoted crystalline silica from Example 13 was tested for its ability to catalyze the methylation of toluene at 500° to 550° C. employing toluene and methanol along with a feed of hydrogen (H$_2$/HC=0.8). The weight hourly space velocity was 3.9 hr$^{-1}$. The results and reaction conditions are shown in Table 12.

TABLE 12

| Ex. No. | SiO$_2$ Coating Weight Percent | Tol MeOH | Temp. °C. | Mole Percent Conversion Toluene | Mole Percent Conversion MeOH | Percent Para Selectivity In Xylene |
|---|---|---|---|---|---|---|
| 70 | 0.3 | 3 | 500 | 17.1 | 99 | 89 |
| 71 | 0.3 | 3 | 500 | 21.0 | 99 | 86 |
| 72 | 1.5 | 10 | 500 | 8.4 | 98 | 83 |
| 73 | 1.5 | 10 | 550 | 9.4 | 98 | 81 |
| 74 | 5.0 | 10 | 500 | 8.4 | 99 | 93 |
| 75 | 5.0 | 10 | 550 | 9.6 | 99 | 91 |

EXAMPLES 76–77

An amount of 1.8 g of the catalyst of Example 15 was employed in two successive methylations of toluene to para-xylene. A 10/1 mole ratio of toluene to methanol, together with a concurrent hydrogen feed in a mole ratio of H$_2$ to hydrocarbon of 0.8, was passed over the ⅛ in molded extrudate catalyst at 101 kPa. The reaction conditions and results expressed in mole percent are summarized in Table 13.

TABLE 13

| Ex. No. | Weight Hourly Space Velocity | Temp. °C. | Mole Percent Conversion Toluene | Mole Percent Conversion MeOH | Percent Para Selectivity in Xylene |
|---|---|---|---|---|---|
| 76 | 7.8 | 550 | 7.5 | 94 | 94 |
| 77 | 11.6 | 550 | 6.0 | 85 | 95 |

EXAMPLES 78–79

An amount of 1.8 g of the catalyst of Example 16 was placed in a 1 inch diameter quartz reactor inserted in a split-tube furnace and employed in two successive methylations of toluene to para-xylene. A 10/1 mole ratio of toluene to methanol, together with a concurrent hydrogen (H$_2$) feed in a mole ratio of H$_2$ to hydrocarbon (HC) of 0.8, was passed over the powder catalyst at 101 kPa (1 atm). The reaction conditions and results expressed in mole percent are summarized in Table 14.

TABLE 14

| Ex. No. | Toluene MeOH | Weight Hourly Space Velocity | Temp. °C. | Mole Percent Conversion Toluene | Mole Percent Conversion MeOH | Percent Para Selectivity in Xylene |
|---|---|---|---|---|---|---|
| 78 | 10/1 | 7.8 | 500 | 7.4 | 98 | 90 |
| 79 | 10/1 | 7.8 | 550 | 8.4 | 99 | 88 |

EXAMPLES 80–81

An amount of 1.8 g of the catalyst of Example 14 was employed in two successive methylations of toluene to para-xylene. A 10/1 mole ratio of toluene to methanol, together with a co-feed of hydrogen, in a mole ratio of hydrogen to hydrocarbon of 0.8 was passed over the powder catalyst at 101 kPa. The reaction conditions and results expressed in mole percent are summarized in Table 15.

TABLE 15

| Ex. No. | Weight Hourly Space Velocity | Temp. °C. | Mole Percent Conversion Toluene | Mole Percent Conversion MeOH | Percent Para Selectivity in Xylene |
|---|---|---|---|---|---|
| 80 | 7.8 | 500 | 8.2 | 99 | 99 |
| 81 | 7.8 | 550 | 7.9 | 99 | 99 |

EXAMPLES 82–84

Six grams of the silica prepared according to Example 1 were added to a solution containing 5.25 g each of the metal salt shown in Table 16 in 15 ml H$_2$O. The mixture was dried in an oven at 110° C. then heated at 250° C. for 2 hrs followed by additional heating at 600° C. for 16 hrs. A methylation was run according to Example 20. The results are given in Table 16.

TABLE 16

| Ex. No. | Salt | Weight Hourly Space Velocity | Temp. °C. | Mole Percent Conversion Toluene | Mole Percent Conversion MeOH | Percent Para Selectivity in Xylene |
|---|---|---|---|---|---|---|
| 82 | Mg (Acetate) | 3.8 | 575 | 2.0 | 89.4 | 87 |
| 83 | Ca (Acetate) | 6.6 | 550 | 5.4 | 99.1 | 86 |
| 84* | Sr (Nitrate) | 3.8 | 575 | 4.4 | 65.3 | 91 |

*1.3 grams of salt were employed

EXAMPLES 85-88

The metal salts were dry blended on a roller mill for 2 hrs with the amount of silica prepared according to Example 1 as shown in Table 17. The mixture was then heated at 250° C. for 2 hrs followed by additional heating at 600° C. for 16 hrs. A methylation was run according to Example 20. The results are reported in Table 17.

TABLE 17

| Ex. No. | Silica Amount (gms) | Salt Type | Salt Amount (gms) | Weight Hourly Space Velocity | Temp. °C. | Mole Percent Conversion Toluene | Mole Percent Conversion MeOH | Percent Para Selectivity in Xylene |
|---|---|---|---|---|---|---|---|---|
| 85 | 6.0 | Ca (Acetate) | 2.6 | 3.8 | 575 | 4.7 | 100 | 95 |
| 86 | 6.0 | Ca (Acetate) | 1.3 | 3.8 | 575 | 7.1 | 100 | 91 |
| 87 | 5.0 | Ba (Acetate) | 2.8 | 3.8 | 575 | 1.6 | 42 | 86 |
| 88 | 5.0 | Ba (Acetate) | 1.4 | 6.6 | 575 | 7.3 | 100 | 76 |

I claim:

1. A process for preparing a promoted crystalline silica catalyst comprising contacting crystalline silica with a member selected from the group consisting of arsenic oxide, phosphorus oxide, magnesium oxide, boron oxide, antimony oxide, amorphous silica, alkaline earth metal oxides, alkaline earth metal carbonates and mixtures and precursors of the foregoing, and thermally activating the resulting crystalline silica/promoter combination.

2. A process according to claim 1 wherein the amorphous silica precursor is selected from the group consisting of ethylorthosilicate and phenylmethylsilicone.

3. A crystalline silica polymorph having essentially clear intracrystalline channels, axes in the range 5.0–6.5 Angstrom units and a density in the range 1.81–1.94 gms/ml.

4. The silica of claim 3, wherein the width at one-half height of the diffraction peak at $d(\text{Å}) = 3.00 \pm 0.05$ under X-ray diffraction is in the range of about $0.05°$–$0.210°$ ($2\theta$).

5. The silica of claim 3 wherein the crystallinity of the silica as measured by peak to background ratio at $d(\text{Å}) = 3.85 \pm 0.03$ is at least 20.0.

6. The silica of claim 3 having a density in the range 1.83–1.89 gms/ml.

7. The silica of claim 4 wherein width at one-half height of the diffraction peaks at $d(\text{Å}) = 3.00 \pm 0.05$ and $1.46 \pm 0.05$ under X-ray diffraction is in the range of about $0.210°$–$0.05°$ ($2\theta$) and $0.320°$–$0.05°$ ($2\theta$), respectively.

8. The silica of claim 6 wherein the peak to background ratio is at least 30.0.

9. The silica of claim 5 having a density in the range 1.83–1.89 gms/ml.

10. The silica of claims 3, 4, 5, 6, 7, 8 or 9 promoted by a member selected from the group consisting of arsenic oxide, phosphorus oxide, magnesium oxide, boron oxide, antimony oxide, amorphous silica, alkaline earth metal oxides, alkaline earth metal carbonates and mixtures and precursors of the foregoing.

* * * * *

UNITED STATES PATENT OFFICE
CERTIFICATE OF CORRECTION

PATENT NO. : 4,283,306
DATED : August 11, 1981
INVENTOR(S) : Frank E. Herkes

It is certified that error appears in the above-identified patent and that said Letters Patent are hereby corrected as shown below:

Column 18, line 4, change "(A)" to -- (Å) --.

Signed and Sealed this

Twenty-seventh Day of October 1981

[SEAL]

Attest:

GERALD J. MOSSINGHOFF

Attesting Officer     Commissioner of Patents and Trademarks